(12) United States Patent
Haham Hay

(10) Patent No.: US 11,875,937 B2
(45) Date of Patent: *Jan. 16, 2024

(54) LIGHTWEIGHT ASYMMETRIC ARRAY OF MAGNET ELEMENTS

(71) Applicant: Epsitau Ltd., Tel Aviv (IL)

(72) Inventor: Noam Haham Hay, Ariel (IL)

(73) Assignee: Epsitau Ltd., Tel Aviv (IL)

( * ) Notice: Subject to any disclaimer, the term of this patent is extended or adjusted under 35 U.S.C. 154(b) by 353 days.

This patent is subject to a terminal disclaimer.

(21) Appl. No.: 17/295,456

(22) PCT Filed: Nov. 10, 2019

(86) PCT No.: PCT/IB2019/059646
§ 371 (c)(1),
(2) Date: May 20, 2021

(87) PCT Pub. No.: WO2020/109896
PCT Pub. Date: Jun. 4, 2020

(65) Prior Publication Data
US 2021/0405138 A1 Dec. 30, 2021

Related U.S. Application Data

(60) Provisional application No. 62/795,575, filed on Jan. 23, 2019, provisional application No. 62/772,638, filed on Nov. 29, 2018.

(51) Int. Cl.
*G01R 33/38* (2006.01)
*H01F 7/02* (2006.01)
(Continued)

(52) U.S. Cl.
CPC .............. *H01F 7/021* (2013.01); *A61B 5/055* (2013.01); *G01R 33/3802* (2013.01);
(Continued)

(58) Field of Classification Search
CPC .. H01F 7/0247; H01F 7/0273; G01R 33/3802
(Continued)

(56) References Cited

U.S. PATENT DOCUMENTS 3,237,059 A * 2/1966 Meyerer ............... H01J 23/087
315/5.35
4,998,084 A 3/1991 Aff
(Continued)

FOREIGN PATENT DOCUMENTS

CN 105390229 A1 3/2016
CN 106257602 A 12/2016
(Continued)

OTHER PUBLICATIONS

Ren et al., "Magnet Array for a Portable Magnetic Resonance Imaging System", IEEE RTT-S International Microwave Workshop Series on RF and Wireless Technologies for Biomedical and Healthcare Applications (IMWS-BIO), pp. 92-95, Sep. 21-23, 2015.
(Continued)

*Primary Examiner* — Alexander Talpalatski

(57) ABSTRACT

A magnet array (700) includes multiple magnet rings (711-720) and a frame. The multiple magnet rings are positioned along a longitudinal axis and coaxially with the longitudinal axis, wherein at least one (712, 713, 719) of the magnet rings possesses rotational symmetry and has both a finite component of magnetization along an azimuthal (θ) coordinate, and a finite magnetization in a longitudinal-radial plane. The multiple magnet rings configured to jointly generate a magnetic field along a direction parallel to the longitudinal axis. The frame is configured to fixedly hold the multiple magnet rings in place.

22 Claims, 5 Drawing Sheets

(51) Int. Cl.
  *H01F 41/02* (2006.01)
  *A61B 5/055* (2006.01)
  *G01R 33/383* (2006.01)

(52) U.S. Cl.
  CPC ......... *G01R 33/383* (2013.01); *H01F 7/0247* (2013.01); *H01F 7/0252* (2013.01); *H01F 7/0273* (2013.01); *H01F 7/0278* (2013.01); *H01F 41/0253* (2013.01)

(58) Field of Classification Search
  USPC .......................................................... 335/306
  See application file for complete search history.

(56) References Cited

U.S. PATENT DOCUMENTS

| | | | |
|---|---|---|---|
| 5,014,032 A * | 5/1991 | Aubert | H01F 7/0278 324/318 |
| 5,028,903 A * | 7/1991 | Aubert | H01F 7/0278 324/318 |
| 5,084,690 A | 1/1992 | Leupold | |
| 5,332,971 A | 7/1994 | Aubert | |
| 5,574,417 A | 11/1996 | Dorri et al. | |
| 5,576,679 A * | 11/1996 | Ohashi | H01J 23/10 315/5.35 |
| 5,581,220 A * | 12/1996 | Rodenbush | H01F 6/06 505/211 |
| 5,659,250 A | 8/1997 | Domigan et al. | |
| 5,717,333 A | 2/1998 | Frese et al. | |
| 5,801,609 A | 9/1998 | Laskaris et al. | |
| 5,900,793 A | 5/1999 | Katznelson et al. | |
| 6,157,278 A | 12/2000 | Katznelson et al. | |
| 6,157,281 A * | 12/2000 | Katznelson | G01R 33/3806 324/319 |
| 6,163,240 A | 12/2000 | Zuk et al. | |
| 6,281,775 B1 | 8/2001 | Rapoport | |
| 6,317,618 B1 | 11/2001 | Livni et al. | |
| 6,333,630 B1 | 12/2001 | Holsinger et al. | |
| 6,411,187 B1 * | 6/2002 | Rotem | G01R 33/3806 335/298 |
| 6,489,872 B1 | 12/2002 | Fukushima et al. | |
| 6,518,867 B2 | 2/2003 | Askaris et al. | |
| 6,534,984 B2 | 3/2003 | Westphal | |
| 7,365,623 B2 | 4/2008 | Xia | |
| 7,423,431 B2 | 9/2008 | Amm et al. | |
| 7,495,441 B2 | 2/2009 | Amor et al. | |
| 7,646,274 B2 | 1/2010 | Rapoport | |
| 7,898,257 B2 | 3/2011 | Katznelson | |
| 8,358,190 B1 | 1/2013 | Hoff et al. | |
| 8,604,794 B2 | 12/2013 | Rapoport | |
| 8,773,230 B2 | 7/2014 | Sakellariou et al. | |
| 8,798,715 B2 | 8/2014 | Rapoport | |
| 9,128,167 B2 | 9/2015 | Sakellariou et al. | |
| 9,297,874 B2 | 3/2016 | Rapoport | |
| 9,482,643 B2 | 11/2016 | Rapoport et al. | |
| 9,562,956 B2 | 2/2017 | Rapoport | |
| 9,770,188 B2 | 9/2017 | Rapoport et al. | |
| 9,910,115 B2 * | 3/2018 | Wald | G01R 33/383 |
| 9,952,294 B2 | 4/2018 | Eskowitz | |
| 10,018,694 B2 | 7/2018 | Vidarsson | |
| 10,076,266 B2 | 9/2018 | Rapoport et al. | |
| 10,426,376 B2 | 10/2019 | Rapoport | |
| 10,679,781 B1 * | 6/2020 | Haham Hay | H01F 7/0247 |
| 10,690,738 B1 * | 6/2020 | Haham Hay | G01R 33/3802 |
| 10,867,733 B2 * | 12/2020 | Haham Hay | H01F 7/0273 |
| 2002/0097122 A1 | 7/2002 | Rapoport | |
| 2011/0291781 A1 | 1/2011 | Sakellariou et al. | |
| 2011/0234347 A1 | 9/2011 | Rapoport | |
| 2011/0248715 A1 | 10/2011 | Telemariam et al. | |
| 2012/0013338 A1 | 1/2012 | Sakellariou et al. | |
| 2012/0098630 A1 | 4/2012 | Sakellariou et al. | |
| 2013/0193973 A1 | 8/2013 | Aubert | |
| 2014/0111202 A1 | 4/2014 | Wald et al. | |
| 2014/0128725 A1 | 5/2014 | Rapoport | |
| 2015/0208994 A1 | 7/2015 | Rapoport | |
| 2015/0285882 A1 | 10/2015 | Mezrich et al. | |
| 2015/0335261 A1 | 11/2015 | Rapoport | |
| 2017/0188879 A1 | 7/2017 | Rapoport | |
| 2017/0276747 A1 | 9/2017 | Hugon et al. | |
| 2017/0300622 A1 | 10/2017 | Laviolette | |
| 2018/0313920 A1 | 11/2018 | Sotgiu | |

FOREIGN PATENT DOCUMENTS

| | | |
|---|---|---|
| CN | 106710781 B | 3/2018 |
| DE | 202012104183 U1 | 2/2013 |
| DE | 202013101097 U1 | 3/2013 |
| DE | 202013103969 U1 | 9/2013 |
| DE | 202013105276 U1 | 12/2013 |
| EP | 1893986 A1 | 3/2008 |
| EP | 2762927 A1 | 8/2014 |
| EP | 2837948 A1 | 2/2015 |
| EP | 2840409 A1 | 2/2015 |
| EP | 3066499 A1 | 9/2016 |
| EP | 3068297 A2 | 9/2016 |
| JP | H0283903 A | 3/1990 |
| JP | H02501001 A | 4/1990 |
| JP | H02501002 A | 4/1990 |
| JP | H06007316 A | 1/1994 |
| JP | H06224027 A | 8/1994 |
| JP | H10064721 A | 3/1998 |
| JP | 2001511597 A | 8/2001 |
| JP | 2001517510 A | 10/2001 |
| JP | 2005253845 A | 9/2005 |
| JP | 2008545492 A | 12/2008 |
| JP | 2009066399 A | 4/2009 |
| JP | 2012530574 A | 12/2012 |
| JP | 2013532496 A | 8/2013 |
| JP | 2018110865 A | 7/2018 |
| WO | 2007120057 A1 | 10/2007 |
| WO | 2010122551 A1 | 10/2010 |
| WO | 2011023913 A1 | 3/2011 |
| WO | WO2012086644 A1 | 5/2014 |
| WO | 201575709 A2 | 5/2015 |
| WO | 2017134635 A1 | 8/2017 |
| WO | 2017165801 A1 | 9/2017 |
| WO | 201842428 A1 | 3/2018 |
| WO | 2020109895 A1 | 6/2020 |

OTHER PUBLICATIONS

Vogel et al., "Rotatable Small Permanent Magnet Array for Ultra-Low Field Nuclear Magnetic Resonance Instrumentation", PLOS One, pp. 1-24, Jun. 6, 2016.

Sakellariou et al., "Permanent magnet assembly producing a strong tilted homogeneous magnetic field: towards magic angle field spinning NMR and MRI", Magnetic Resonance Chemistry, vol. 48, pp. 903-908, Sep. 30, 2010.

Ren et al., "An Aubert Ring Aggregate Magnet Helmet for 3D Head Imaging in a Low-field Portable MRI", Proceedings of the International Society for Magnetic Resonance in Medicine, ISMRM, 27 Annual Meeting and Exhibition, No. 1545, pp. 1-3, May 11-16, 2019.

Hugon et al., "Design, fabrication and evaluation of a low-cost homogeneous portable permanent magnet for NMR and MRI", C. R. Chimie 13 , pp. 388-393, year 2010.

Blümler et al., "Hardware Developments: Halbach Magnet Arrays", New Developments in NMR No. 5, Royal Society of Chemistry, pp. 133-157, year 2016.

Chou et al., "Simple method for the generation of multiple homogeneous field vols. inside the bore of superconducting magnets", Nature Scientific Reports, pp. 1-6, Jul. 17, 2015.

Cooley et al., "Design of Sparse Halbach Magnet Arrays for Portable MRI Using a Genetic Algorithm", IEEE Transactions on Magnetics, vol. 54, No. 1, pp. 1-12, Jan. 2018.

Demas et al., "Compact Magnets for Magnetic Resonance", Wiley Periodicals, Inc, pp. 48-59, year 2009.

Manz et al., "A mobile one-sided NMR sensor with a homogeneous magnetic field: The NMR-MOLE", Journal of Magnetic Resonance, issue 183, pp. 25-31, year 2006.

(56) References Cited

OTHER PUBLICATIONS

Ren et al., "Design and Optimization of a Ring-Pair Permanent Magnet Array for Head Imaging in a Low-Field Portable MRI System", IEEE Transactions on Magnetics, pp. 1-8, year 2018.
International Application # PCT/IB2019/059645 Search Report dated Feb. 21, 2020.
International Application # PCT/IB2019/059646 Search Report dated Feb. 21, 2020.
"Notice of reasons for refusal" for JP2021530283, dated Aug. 25, 2023, 10 pages (with English translation).
"Notice of allowance" for JP2021530283, dated Sep. 8, 2023, 6 pages (with English translation).

* cited by examiner

LIGHTWEIGHT ASYMMETRIC ARRAY OF MAGNET ELEMENTS

CROSS-REFERENCE TO RELATED APPLICATIONS

This application claims the benefit of U.S. Provisional Patent Application 62/772,638, filed Nov. 29, 2018, and U.S. Provisional Patent Application 62/795,575, filed Jan. 23, 2019, whose disclosures are incorporated herein by reference.

FIELD OF THE INVENTION

The present invention relates generally to magnet assemblies, and particularly to lightweight magnet assemblies comprising permanent magnets and design methods thereof.

BACKGROUND OF THE INVENTION

Designs of permanent magnet arrays aiming at achieving a strong and uniform magnetic field have been previously reported in the patent literature. For example, U.S. Pat. No. 7,423,431 describes a permanent magnet assembly for an imaging apparatus having a permanent magnet body having a first surface and a stepped second surface which is adapted to face an imaging volume of the imaging apparatus, wherein the stepped second surface contains at least four steps.

As another example, U.S. Pat. No. 6,411,187 describes adjustable hybrid magnetic apparatus for use in medical and other applications includes an electromagnet flux generator for generating a first magnetic field in an imaging volume, and permanent magnet assemblies for generating a second magnetic field superimposed on the first magnetic field for providing a substantially homogenous magnetic field having improved magnitude within the imaging volume. The permanent magnet assemblies may include a plurality of annular or disc like concentric magnets spaced-apart along their axis of symmetry. The hybrid magnetic apparatus may include a high magnetic permeability yoke for increasing the intensity of the magnetic field in the imaging volume of the hybrid magnetic apparatus.

U.S. Pat. No. 10,018,694 describes a magnet assembly for a magnetic resonance imaging (MRI) instrument, the magnet assembly comprising a plurality of magnet segments that are arranged in two or more rings such that the magnet segments are evenly spaced apart from adjacent magnet segments in the same ring, and spaced apart from magnet segments in adjacent rings. According to an embodiment, a plurality of magnet segments is arranged in two or more rings with the magnetization directions of at least some of the magnet segments being unaligned with a plane defined by their respective ring, to provide greater control over the resulting magnetic field profile.

U.S. Pat. No. 5,900,793 describes assemblies consisting of a plurality of annular concentric magnets spaced-apart along their axis of symmetry, and a method for constructing such assemblies using equiangular segments that are permanently magnetized.

SUMMARY OF THE INVENTION

An embodiment of the present invention provides a magnet array including multiple magnet rings and a frame. The multiple magnet rings are positioned along a longitudinal axis and coaxially with the longitudinal axis, wherein at least one of the magnet rings possesses rotational symmetry and has both a finite component of magnetization along an azimuthal ($\theta$) coordinate, and a finite magnetization in a longitudinal-radial plane. The multiple magnet rings configured to jointly generate a magnetic field along a direction parallel to the longitudinal axis. The frame is configured to fixedly hold the multiple magnet rings in place.

In some embodiments, the multiple magnet rings, including the at least one magnet ring possessing rotational symmetry and having the finite component of magnetization along the azimuthal ($\theta$) coordinate, are configured to jointly generate the magnetic field with at least a given level of uniformity inside a predefined inner volume.

In some embodiments, the multiple magnet rings, including the at least one magnet ring having the finite component of magnetization along the azimuthal ($\theta$) coordinate, are configured to jointly minimize a fringe field outside the magnet array.

In an embodiment, each magnet ring has a rotational symmetry with respect to an in-plane rotation of the ring around the longitudinal axis.

In another embodiment, at least one of the magnet rings encircles the predefined inner volume, wherein a minimal inner radius of the magnet rings positioned on one side of a center of the inner volume along the longitudinal axis is different from the minimal radius of the magnet rings positioned on the other side of the center of inner volume.

In some embodiments, the magnet rings are arranged with reflectional asymmetry with respect to the longitudinal axis.

In some embodiments, the inner volume is an ellipsoid of revolution around the longitudinal axis.

In an embodiment, the at least one magnet ring that has the finite component of magnetization along the azimuthal ($\theta$) coordinate is made as a single solid element. In another embodiment, the at least one magnet ring that has the finite component of magnetization along the azimuthal ($\theta$) coordinate is made as a segmented ring with equally spaced identical segments.

In some embodiments, each of the magnet rings has a shape including one of an ellipse, a circle, and a polygon.

In some embodiments, the magnet array further includes one or more additional arrays of magnet rings, wherein the magnet rings in the additional arrays are coaxial with respective longitudinal axes that are set at respective angles from the longitudinal axis.

There is additionally provided, in accordance with an embodiment of the present invention, a method for producing a magnet array, the method including positioning multiple magnet rings along a longitudinal axis and coaxially with the longitudinal axis, wherein at least one of the magnet rings possess a rotational symmetry and has both a finite component of magnetization along an azimuthal ($\theta$) coordinate, and a finite magnetization in a longitudinal-radial plane, with the multiple magnet rings configured to jointly generate a magnetic field along a direction parallel to the longitudinal axis. The multiple magnet rings are fixedly held in place using a frame.

The present invention will be more fully understood from the following detailed description of the embodiments thereof, taken together with the drawings in which:

DETAILED DESCRIPTION OF EMBODIMENTS

Overview

Figure 1:
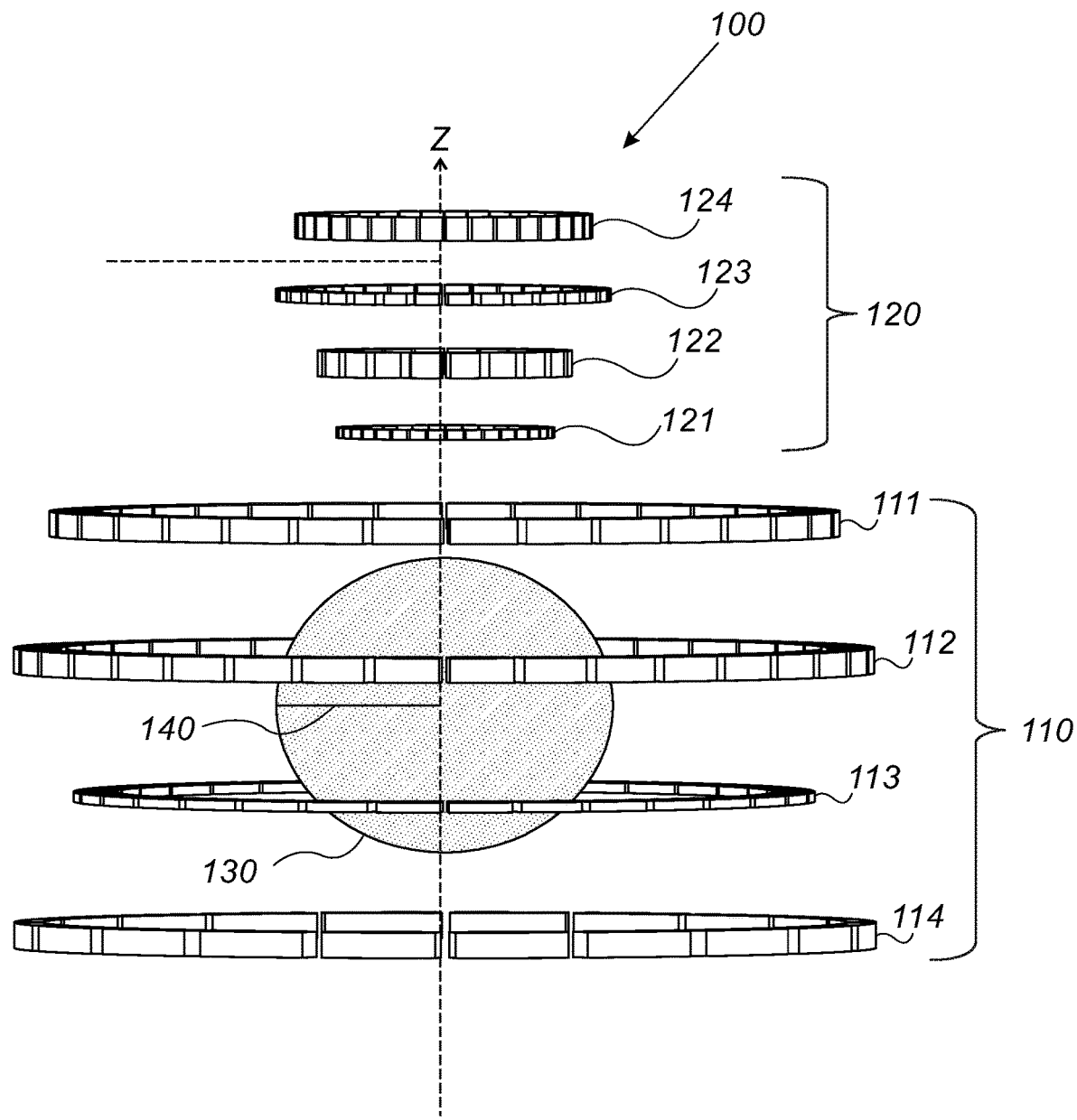
FIG. 1 is a perspective view of an asymmetric magnet array comprising a first magnet assembly and a second magnet assembly, according to an embodiment of the present invention.

Magnetic fields that are strong and uniform are needed in a wide variety of disciplines, spanning medicine, aerospace, electronics, and automotive industries. As an example, magnets used in Magnetic Resonance Imaging (MRI) of the human brain typically provide a magnetic field with a strength of 0.1 to 3 Tesla, which is uniform to several parts per million (ppm) inside an imaging volume of approximately 3000 cubic centimeters, e.g. the interior of a sphere of radius 9 cm. However, such magnets have limited applications due to their considerable size and weight. Moreover, in general with magnet designs, there is a severely limiting trade-off between weight, magnetic field uniformity, and a size of a volume inside which a given uniformity can be achieved.

Embodiments of the present invention that are described hereinafter provide lightweight permanent magnet arrays that generate strong and uniform magnetic fields (e.g., in the range of 0.1 to 1 Tesla). Some of the disclosed magnet arrays are configured for emergency-care brain mobile MRI systems, such as a head MRI system inside an ambulance. Generally, however, the disclosed techniques can be applied in any other suitable system.

In the description herein, using a cylindrical reference frame consisting of longitudinal (Z), radial (r), and azimuthal (θ) coordinates, an inner volume is defined as a volume of an ellipsoid of revolution around the longitudinal axis. Examples of an inner volume are a prolate having its long axis along the longitudinal axis, and an oblate having its short axis along the longitudinal axis. A lateral plane is further defined as any r-θ plane (i.e., a plane orthogonal to the longitudinal z-axis). A particular definition of an inner volume is an imaging volume of an MRI system inside which the magnetic field has at least a given level of uniformity.

In some embodiments of the present invention, a magnet array is provided that comprises a frame, which is configured to hold, fixed in place, multiple magnet rings coaxial with a central longitudinal axis at different positions along the axis, wherein the magnet rings lie in lateral planes with at least one ring encircling an area contained in an inner volume through which the longitudinal axis passes (i.e., the ring intersects the inner volume). In the present description a frame is defined by its mechanical capability to hold the rings in place, and which can be made in various ways, for example, using a yoke or by embedding the rings in a surrounding material (e.g., in epoxy).

The multiple magnet rings are arranged with reflectional asymmetry with respect to the longitudinal axis. In the context of the present disclosure and in the claims, the term "reflectional asymmetry with respect to the longitudinal axis" means that no plane perpendicular to the longitudinal axis is a plane of symmetry for the magnet array. In other words, the magnet array is not symmetric under flipping with respect to the longitudinal axis at any point along the axis. Reflectional asymmetry is also referred to as point asymmetry or mirror-image asymmetry. For brevity, any reference to "asymmetry" of the magnet array in the description below means the reflectional asymmetry defined above.

The multiple magnet rings are configured to jointly generate a magnetic field along a direction parallel to the longitudinal axis of at least a given level of uniformity inside the inner volume. The magnet array has each magnet ring generate a magnetic field having a rotational symmetry (continuous or discrete) with respect to an in-plane rotation of the ring around the longitudinal axis.

In some embodiments, each of the magnet rings of any of the disclosed magnet arrays has a shape comprising one of an ellipse, most commonly a circle, or of a polygon. The magnet rings are each made of either a single solid element or an assembly of discrete magnet segments. The magnet rings are pre-magnetized with a magnetization direction which is designed to maximize the uniformity of the magnetic field inside the inner volume and optionally minimize the safety zone defined by the area around the magnet for which the magnetic field exceeds 5 gauss.

In some embodiments, which are typically configured for head MRI applications, a disclosed asymmetric permanent magnet array can be described as comprising a first magnet assembly, comprising two or more magnet rings having a first inner diameter, and a second magnet assembly, comprising two or more magnet rings having a second inner diameter. The first inner diameter is larger than the maximal lateral diameter of the imaging volume and the second inner diameter is smaller than or equal to the maximal lateral diameter of the imaging volume.

Typically, the magnet rings lie in different longitudinal axis positions. The second magnet assembly is asymmetrically placed relative to the imaging volume. The asymmetric structure of the disclosed magnet array is thus optimized to fit a human head, in which physical access to an inner volume (which is the same as the imaging volume) containing the brain is through the first assembly but not the second. The first and second magnet assemblies are configured to jointly generate a magnetic field parallel to the longitudinal axis of at least a given level of uniformity inside the inner volume.

In some embodiments, a magnet array is provided that includes at least one magnet ring, which is rotationally symmetric and characterized by magnetization components $M=(M_r, M_\theta, M_z)$, having a finite component of magnetization along the azimuthal (θ) coordinate (i.e., a non-zero azimuthal projection of the magnetization) in addition to having a finite component (i.e., non-zero projection of the magnetization) of the magnetization in a longitudinal-radial plane. Such a magnet ring is named hereinafter "theta magnetic ring." Including at least one such theta magnetic ring in the asymmetric array can improve uniformity inside the inner volume compared with that achieved by a magnet array of a same weight made solely of rotationally symmetric solid or segmented rings having magnetization solely in a longitudinal-radial plane.

The various types of magnet rings disclosed above are typically made of a strongly ferromagnetic material, such as an alloy of neodymium, iron, and boron (NdFeB), whose Curie temperature is well above the maximum ambient operating temperature. Other material options include ferrites, samarium-cobalt (SmCo) magnets, or any other permanent magnet material. Depending on the design and type of ring, ring segments may have the shape of a sphere, a cylinder, an ellipsoid, or a polygonal prism with shapes such as a cuboid, a wedge, or an angular segment.

The two disclosed techniques to realize magnet arrays (e.g., using an asymmetric geometry, and using a theta magnet ring), separately or combined, enable the use of strong and uniform magnet arrays in applications that specifically require lightweight magnet solutions.

Asymmetric Magnet Array for Head MRI Applications

FIG. 1 is a perspective view of an asymmetric magnet array 100 comprising a first magnet assembly 110 and a second magnet assembly 120, according to an embodiment of the present invention. As seen, first and second magnet assemblies 110 and 120 each comprise at least two magnet rings which are coaxial with a central longitudinal axis, denoted "Z-axis," which passes through an inner volume 130. The multiplicity of magnet rings has variable transverse dimensions and variable displacements along the Z-axis. In FIG. 1, by way of example, first assembly 110 is shown as consisting of four magnet rings, 111-114, and second assembly 120 is shown as consisting of four magnet rings, 121-124. Each of the rings in assemblies 110 and 120 is either a solid ring or a segmented ring, i.e., a ring comprising discrete segments. The segments may have the shape of a sphere, a cylinder, an ellipsoid, or a polygonal prism, preferably cuboids. It will be appreciated that the rings may have any cross section including non-regular shape cross section. All segments belonging to a single ring share a common shape and material composition, as well as the same magnetic moment components in the longitudinal (Z), radial, and azimuthal directions. However, one or more of these characteristics may differ from one ring to another.

In case of a segmented ring, referring to the magnetic moment of a segment means that the segment is uniformly magnetized to a specific direction in space, its radial, longitudinal and azimuthal directions are calculated in the segment center of mass.

In case of a solid ring, M varies continuously in space having azimuthal, radial, and longitudinal components independent of the azimuth coordinate. It will be appreciated that a solid magnet piece with a complex shape may be magnetized in a fashion that $M_r$, $M_\theta$, or $M_Z$ changes as a function of Z, or R, in a gradual or stepped way, creating effectively several rings from a magnetization perspective, although mechanically composed of one continuous piece. In the present context, this sort of implementation is regarded as having multiple rings where their borders are determined by the magnetization perspective, rather than by mechanical segmentation.

The peripheral shape of the rings may be any closed curve, such as a circle, ellipse, or polygon. In some cases, the choice of peripheral shape depends upon the cross-sectional shape of inner volume 130. It will be appreciated that a rotational symmetry of a ring, implies among others, that its peripheral shape is also rotationally symmetric (For example a shape of a circle, or an equiangular-equilateral polygon). In the special case where all rings are circular, the minimal inner radius of rings 111-114 of first assembly 110 is denoted by R1, and the minimal inner radius of rings 121-124 of second assembly 120 is denoted by R2. For a given target radius Ri, which, by way of example, has the lateral radius 140 of inner volume 130 that defines a maximal radius of a spheroid volume inside that is used for imaging and which the magnetic field has at least a given level of uniformity, the values of R1 and R2 satisfy the relationship Ri<R1, and 0≤R2≤Ri. In the case of R2=0, at least one of the rings of second assembly 120 is a solid disc. It is appreciated that assembly 120 may contain rings with inner radius larger than R2 and even larger than R1. The assemblies are separated in the Z direction with a gap which is typically (but not limited to) 0-10 cm. For the present purpose, if a ring extends in Z direction to both assemblies, one part of the ring will be considered as included in the first assembly while the other part in the second assembly. In this case the gap between arrays will be 0.

In an embodiment, in the asymmetric array, the minimal radius of the rings positioned on one side of the center of the inner volume is different from the minimal radius of the rings positioned on the other side of the center. The center of the inner volume can be defined in any suitable way, e.g., the center of the section of the longitudinal axis that lies within the inner volume. In addition, when the inner imaging volume is only partially enclosed by the array the center will be considered as the center of the section of the longitudinal axis that lies within the inner volume and inside the array. An array which obeys the former embodiment may be described as comprised of two sub-assemblies with different minimal inner radiuses as described above.

Inner volume 130 is a simply-connected region at least partially enclosed by assembly 110, which is typically an ellipsoid or a sphere. As shown, the inner volume 130 is enclosed by the magnet array 110, with rings 112-113 encircling inner volume 130. In an embodiment, inner volume 130 is an oblate ellipsoid with semi-axes approximately equal to 0.5 R1, 0.5 R1, and 0.3 R1. The parameters of such rings are not limited to the inner and outer radius of a ring, its Z displacement, or Z-axis thickness. In addition, magnetic moment angles are all optimized using a calculation method such as a finite element, finite difference, or analytical approach, combined with a gradient descent optimization algorithm to achieve the best uniformity, for a given field strength in the imaging volume, with a minimal weight. This is allowed due to the fact that each assembly contains a multiplicity of rings, all of which are optimized.

One aspect of the asymmetry of magnet array 100 is that different rings have different transverse dimensions and magnetic moment directions wherein the rings are arranged in an array having reflectional asymmetry with respect to the longitudinal axis (i.e., are asymmetrical with respect to Z-axis inversion). In the context of the present disclosure and in the claims, the term "reflectional asymmetry with respect to the longitudinal axis" means that no plane perpendicular to the longitudinal axis is a plane of symmetry for the magnet array. In other words, the magnet array is not symmetric under flipping with respect to the longitudinal axis at any point along the axis. Reflectional asymmetry is also referred to as point asymmetry or mirror-image asymmetry. For brevity, any reference to "asymmetry" of the magnet array in the description below means the reflectional asymmetry defined above.

The asymmetry in the design is particularly advantageous when imaging inherently non-symmetrical specimens, such as the human head. For example, in one such case, it has been found that the rings belonging to assembly 110 may be primarily magnetized in a first given direction (e.g., the r-direction), whereas those belonging to assembly 120 may primarily magnetized in another direction (e.g., the z-direction).

Finally, the direction of magnetization of each individual ring may be optimized to obtain both uniformity in the inner volume as well as fringe field reduction so as to create a magnetic circuit which closes the field lines close to the magnet ring. In an embodiment, the discrete magnet segments are each pre-magnetized with a respective magnetization direction that minimizes a fringe field outside the magnet array.

FIGS. 2A and 2B-2D are a perspective view of an asymmetric magnet array 200, and plots of magnetic field lines generated separately and jointly by the assemblies, respectively, according to another embodiment of the present invention. Uniformity is not evident by uniform density of the lines (as lines were drawn denser in the imaging zone for better details) rather by z-axis alignment of the lines.

Figure 2A:
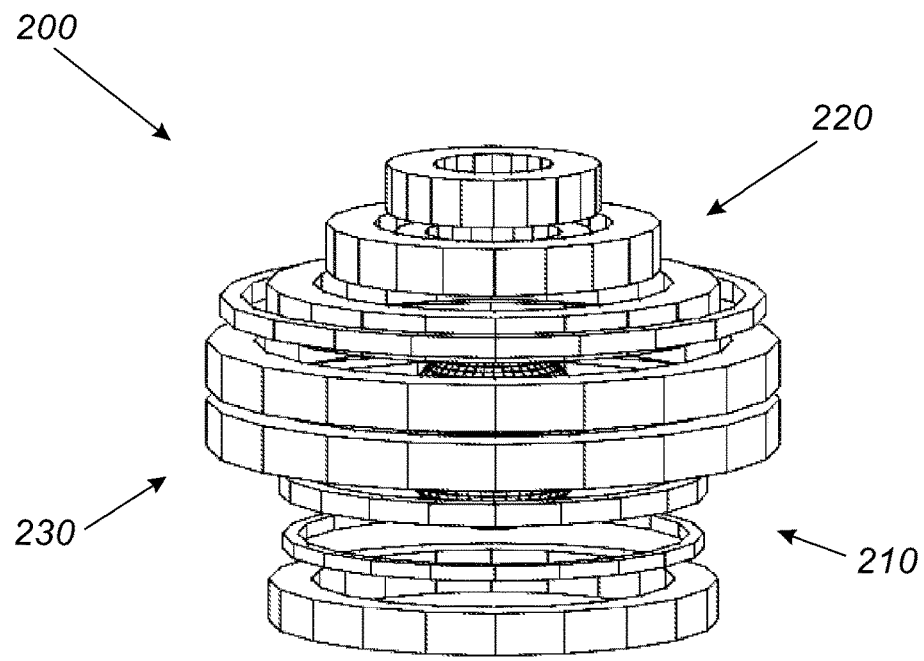
FIGS. 2A and 2B-2D are a perspective view of an asymmetric magnet array, and plots of magnetic field lines generated separately and jointly by the assemblies, respectively, according to another embodiment of the present invention.

As seen in FIG. 2A, an inner volume 230 is a simply-connected region at least partially enclosed by a first magnet assembly 210, which is typically an ellipsoid or a sphere. A second magnet assembly 220 of the asymmetric array, "caps" inner volume 230. As mentioned above, different rings may have different magnetization directions to optimize the uniformity and fringe field of the magnet array. For instance, one ring may have a magnetization vector in a direction substantially different (e.g., by more than 45 degrees) from another ring. For instance, the magnetization vectors of the permanent magnet segments may point primarily in the r direction in one ring, and primarily in the Z direction in another ring. Furthermore, two rings belonging to the same assembly may have substantially different magnetization directions. For instance, one ring of the first assembly may have its magnetization primarily in the r direction, another ring of the first assembly may have its magnetization in primarily the −z direction while a third ring of the first assembly may have its magnetization at −45 degrees in the r−z plane. In an embodiment, the two or more ring have a magnetization vector in a direction different by more than 45 degrees from one another.

In a particular case (not shown) it was found that the rings in assembly 210 are dispersed in their inner radius between 15 cm and 30 cm, and dispersed in their Z position in a length of 25 cm, while the rings in assembly 220 are dispersed in their inner radius between 0.05 cm and 30 cm, and dispersed in their Z position in a length of 12 cm, with the displacement between the two assemblies in the Z direction between 0 cm and 10 cm.

Figure 2B:
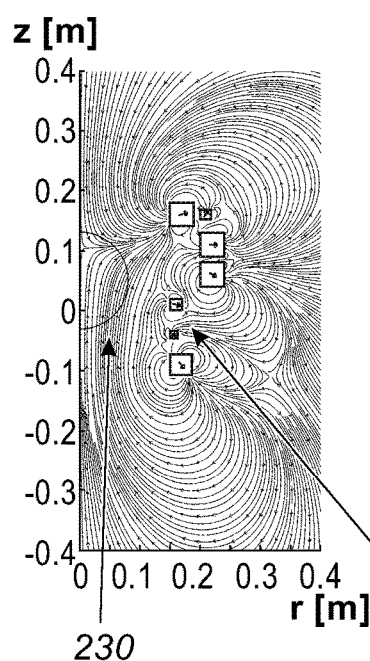

FIG. 2B shows the magnetic field lines of the field generated by first magnet assembly 210 (rings cross-sectionally illustrated by squares, each with a direction of magnetization of the ring in an r−z plane) inside and outside an inner volume 230. As seen, the field lines inside inner volume 230 are largely aligned along the z-axis, however they sharply bend at the top portion of volume 230, where the field becomes exceedingly non-uniform.

Figure 2C:
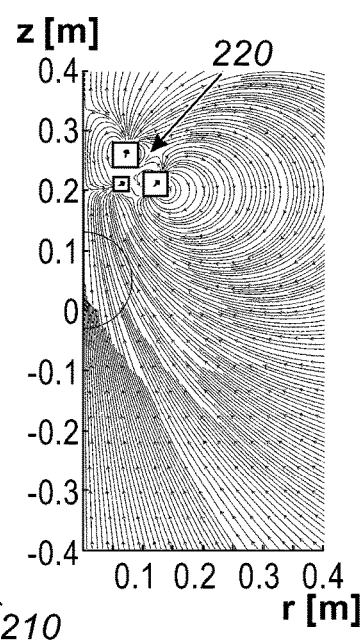

FIG. 2C shows the magnetic field lines of the field generated by second magnet assembly 220 inside and outside an inner volume 230. As also seen here, the field lines inside inner volume 230 are largely aligned along the z-axis. However, they tilt opposite to the field lines of FIG. 2B with respect to the z-axis, and become exceedingly non-uniform at a bottom portion of volume 230.

Figure 2D:
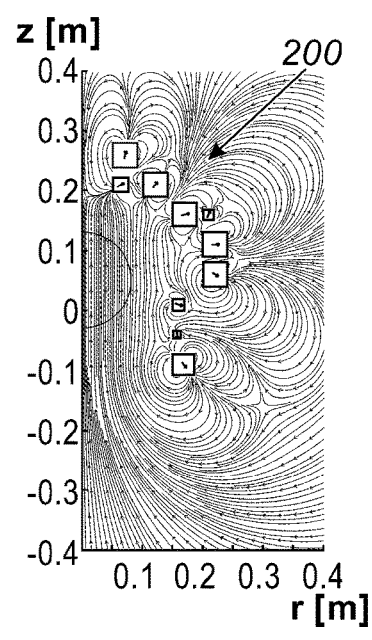

As seen on FIG. 2D, when combined into a full array 200, assemblies 210 and 220 compensate for each other's field non-uniformity, to achieve a uniform magnetic field along the z-axis to a better degree than a prespecified threshold.

FIGS. 2A-2D show an exemplary array containing ten rings. It will be appreciated that the array may contain more rings (e.g. several tens or hundreds of rings) which are all optimized as described above. The more rings contained in the array, the better magnet performance can be achieved (e.g., higher uniformity level, larger magnetic field or larger imaging volume). The improved performance comes with the drawback of increased complexity and production cost of the array due to the large number of elements. Thus, a practitioner skilled in the art should consider the required number of rings according to the specific application.

Figure 3:
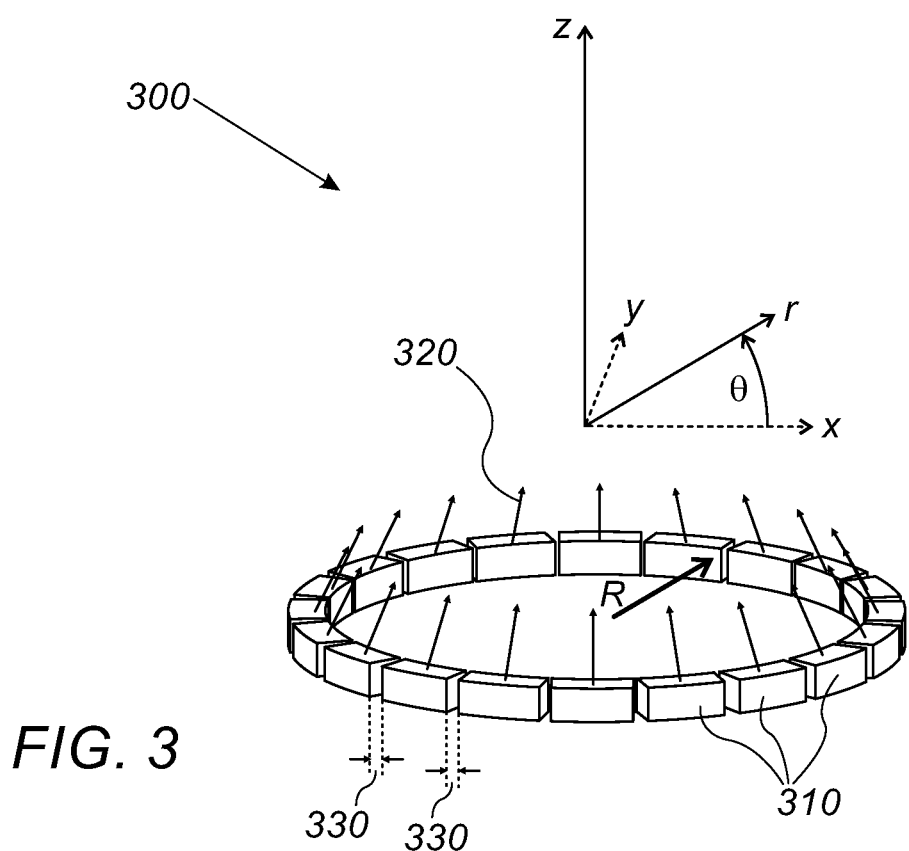
FIG. 3 is a perspective view of a segmented magnet ring, which may be any one of the rings in the magnet arrays of FIGS. 1 and 2, according to an embodiment of the present invention.

FIG. 3 is a perspective view of a single segmented magnet ring 300, which may be any one of the rings in magnet arrays 100 and 200 of FIGS. 1 and 2, according to an embodiment of the present invention. In FIG. 3, each magnet segment 310 has a magnetization vector 320 lying in the r−Z plane, with similar longitudinal (Z) and radial (r) components. Furthermore, each segmented ring possesses rotational symmetry with an azimuthal period equal to 360/N degrees where N is the number of segments in the ring. (For a solid ring, i.e., for N→∞, the rotational symmetry is continuous). In some embodiments, the disclosed rings have rotational symmetry of an order N≥8. It will be appreciated that the disclosed array contains rings with rotational symmetry and hence the result magnetic field is along the longitudinal axis. It is possible however to incorporate in the asymmetric array rings which are non-rotationally symmetric in a fashion that optimizes the fringe field and uniformity in the inner volume. In such a case the magnetic field may be along an arbitrary axis. Although such an array may be substantially worse than a rotationally symmetric array, the use of asymmetry with rings as disclosed may substantially improve uniformity of the array compared to a symmetric one.

Discrete segments 310 are equally spaced and attached to one another using, for example, an adhesive, which is preferably non-electrically conducting, or are held together mechanically with gaps 330 between adjacent segments filled by (but not limited to) a preferably insulating material. It will be appreciated that the rotationally symmetric segmented rings may also include a combination of more than one type of segments. For thermal stability of all of ring 300, it is preferable that the adhesive or gaps consist of a material which is also thermally conductive, such as silicon oxide, silicon nitride, or aluminum oxide. Individual magnet segments 310 may be made of the aforementioned strongly ferromagnetic materials, whose Curie temperature is well above the operating temperature of an associated system that includes such elements as an array 200, e.g., a mobile MRI system.

It will be appreciated that the descriptions in FIGS. 1-3 are intended only to serve as examples, and that many other embodiments are possible within the scope of the present invention. For example, rotation of the magnet moment vector in the r−z−θ plane can be achieved, in an alternative embodiment, by rotating the individual magnet segments 310 through a distinct angle of rotation, which may be different for different rings. Further, magnet arrays 100 and 200 may be combined with either a static or dynamic shimming system, to further improve field uniformity inside inner volumes 130 and 230, respectively. When dynamic shimming or gradient pulse fields are used, the presence of electrically insulating adhesive or empty gaps between adjacent magnet segments 310 helps to minimize the negative effects of eddy currents on field uniformity. Furthermore, magnet arrays 100 and 200 may be combined with resistive coils placed concentric to the z-axis, in order to enhance the magnetic field strength inside inner volumes 130 and 230.

Magnet Array Including Theta Magnet Rings

Figure 4:
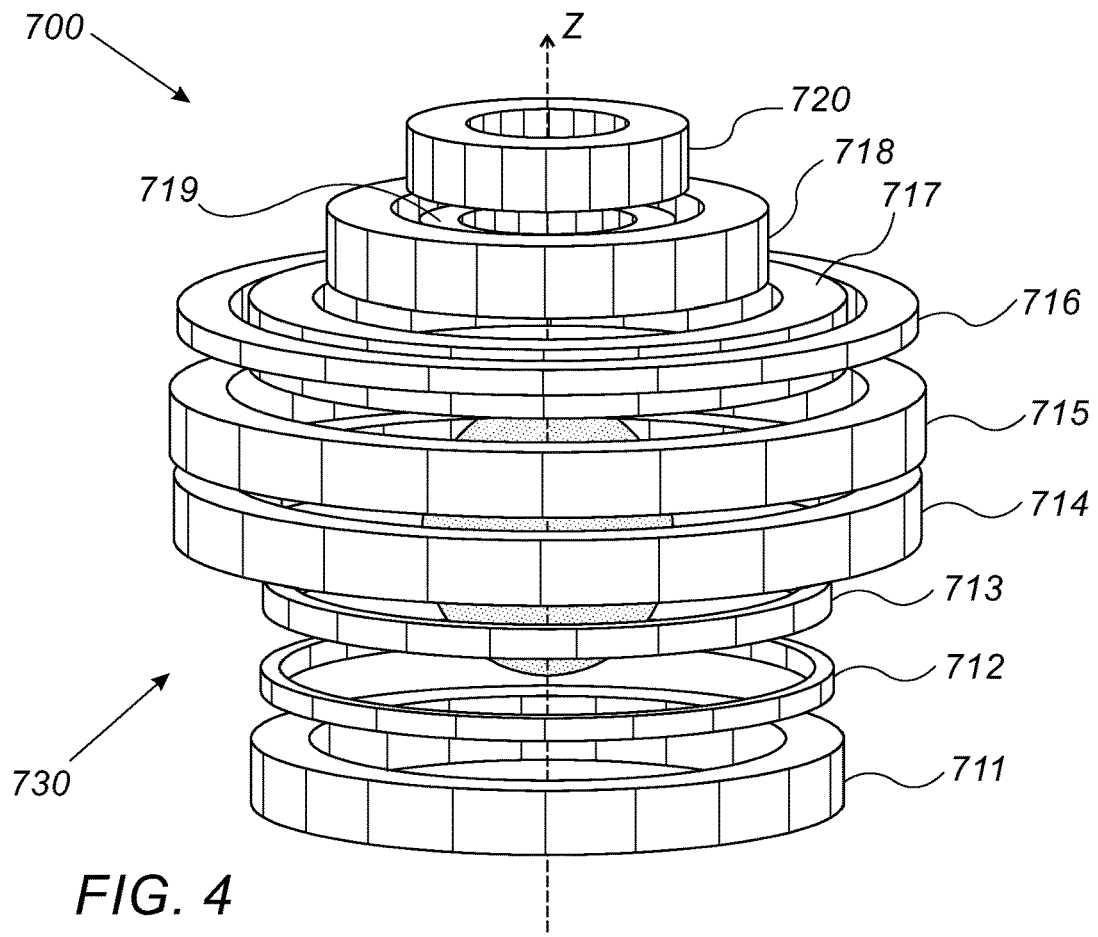
FIG. 4 is a perspective drawing of an asymmetric magnet array comprising three theta magnetic rings, according to an embodiment of the present invention.

FIG. 4 is a perspective drawing of an asymmetric magnet array 700 comprising three theta magnetic rings (712, 713, 719), according to an embodiment of the present invention. By way of example, magnet array 700 comprises ten magnetic rings 711-720 surrounding an axis Z which passes through an inner volume 730. Some of the magnetic rings may be solid, and some may be segmented and optionally have gaps between adjacent magnetic segments. The rings are located at different positions along the Z-axis and, in general, have different transverse dimensions, radial thicknesses, and axial thicknesses.

As in the above shown arrays, magnet array 700 defines a standard cylindrical coordinate system. Each magnetic ring has a magnetization which is rotationally symmetric and characterized by magnetization components $M=(M_r, M_\theta, M_Z)$. All the segments within a given segmented ring have the same magnetization components represented by three components of magnetic moment, $M=(M_r, M_\theta, M_Z)$, in the aforementioned cylindrical reference frame of coordinates. Consequently, each segmented ring possesses rotational symmetry with an azimuthal period equal to 360/N degrees where N is the number of segments in the ring.

In case of a segmented ring, referring to the magnetic moment of a segment means that the segment is uniformly magnetized to a specific direction in space, and its radial, longitudinal and azimuthal directions are calculated in the segment center of mass. In case of a solid ring, M varies continuously in space and has azimuthal, radial, and longitudinal components independent of theta.

The magnetization M is generally different for different rings. At least one of the magnetic rings in the magnet array is a "theta magnetic ring;" that is, it has a non-zero projection of the magnetization in the theta direction ($M_\theta \neq 0$) in addition to a non-zero projection of the magnetization in the r-Z plane. The non-zero projection on the r-Z plane is essential as a magnet ring with only azimuthal magnetization does not produce a substantial magnetic field.

Essentially, the introduction of a non-zero theta component in a given ring has the effect of reducing the relative contribution of that ring to the total magnetic field inside the imaging volume, thus providing extra degrees of freedom which are unrelated to the geometry of the rings. These extra degrees of freedom are most advantageous when the array is subject to various geometric constraints (such as position of the rings, radial/axial thickness), which commonly arouse from mechanical or manufactural limitations. With the aid of computerized magnetic field simulation tools, a designer can adjust, or "tune," the magnitude of the non-zero theta component in the theta magnetic ring(s), together with geometric properties of all the magnetic rings (such as height, outer radius, inner radius, thickness, and z-axis position) so as to achieve a high level of magnetic field uniformity, or a large inner volume, as required, for example for portable head MRI systems.

For example, rings 712, 713, and 719 may be theta rings having magnetization directions in cylindrical coordinates $(M_r, M_\theta, M_Z)$ given by $(0, \sqrt{3}/2, -1/2)$ $(1/\sqrt{3}, 1/\sqrt{3}, -1/\sqrt{3})$, and $(1/\sqrt{2}, 1/\sqrt{2}, 0)$ respectively. In an embodiment, the one or more magnet rings with the finite component of magnetization along the azimuthal (θ) coordinate and the rest of the rings, are configured to jointly generate the magnetic field with at least a given level of uniformity inside the inner volume.

The magnetic segments of magnetic rings 711-715 can be made of the aforementioned strongly magnetic materials. The segments typically are pre-magnetized with specific values for the components of magnetic moment. The shape of the segments may be any of the aforementioned segment shapes (e.g., wedge or angular segment).

The disclosed introduction of a non-zero theta component in the magnetization vector ($M_\theta \neq 0$) of at least one ring in an array of magnetic rings can greatly enhance the uniformity of the magnetic field inside the inner volume of the array, or alternatively, greatly enlarge the inner volume for a given level of uniformity. This advantage applies to solid rings which comprise a solid magnet piece with spatially continuous magnetization. It also applies to segmented magnetic rings with segments which are contiguous with no gaps, as well as to rings whose segments are separated by air gaps or gaps filled with a non-magnetic material. It is appreciated that the gaps may be also filled with materials which are not permanent magnets but has some non-trivial magnetic permeability such as (but not limited to) paramagnets, antiferromagnets, diamagnets, ferromagnets, and ferrimagnets.

Figure 5:
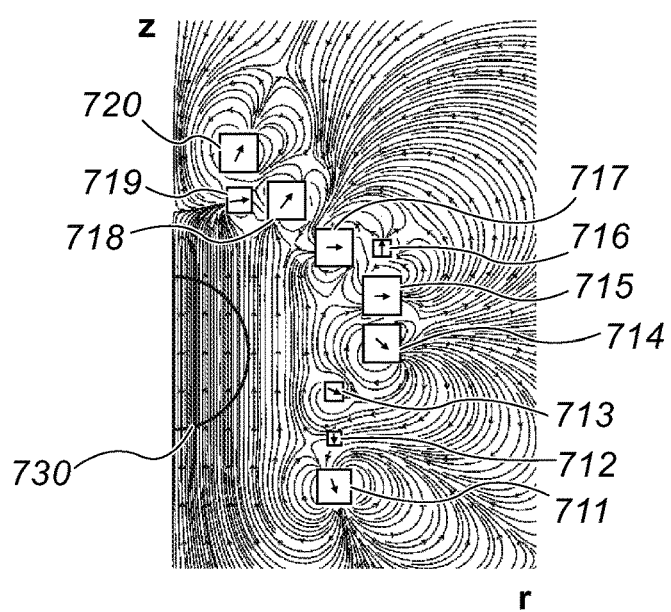
FIG. 5 is a plot of magnetic field lines generated by the magnet array of FIG. 4, according to an embodiment of the present invention.

FIG. 5 is a plot of magnetic field lines generated by magnet array 700 of FIG. 4, according to an embodiment of the present invention. Uniformity is not evident by uniform density of the lines (as lines were drawn denser in the imaging zone for better details) rather by z-axis alignment of the lines. As seen, array 700 achieves a uniform magnetic field along the z-axis with z axis alignment which extends almost to the rings. While not visible, the theta rings improve uniformity. Therefore, including a few theta magnet rings in an asymmetric array of ring magnets may therefore be particularly useful for mobile MRI applications, such as an MRI ambulance.

FIGS. 4 and 5 show an exemplary array containing a total of ten rings, from which three are theta rings. It will be appreciated that the array may contain more theta rings (e.g., several tens or hundreds of rings) which are all optimized as described above. The more theta rings contained in the array, the better magnet performance can be achieved (e.g., higher uniformity level, larger magnetic field or larger imaging volume). The improved performance comes with the drawback of increased complexity and production cost of the array due to the large number of elements. Thus, a practitioner skilled in the art should consider the required number of rings according to the specific application.

Figure 6:
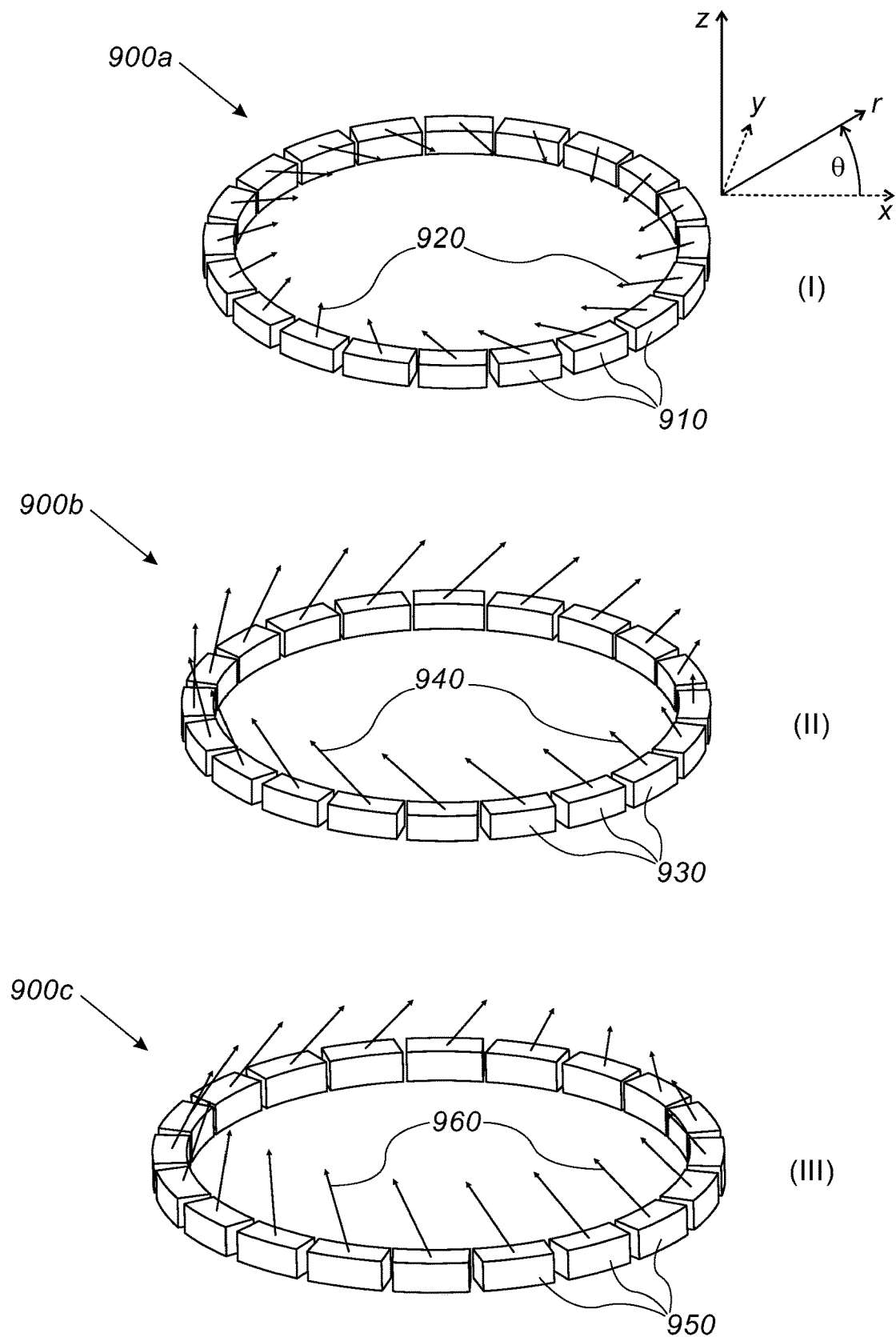
FIG. 6 is a perspective view of theta magnet rings, which may be any one of the rings in the magnet array of FIG. 4, according to embodiments of the present invention.

FIG. 6 is a perspective view of theta magnet rings, which may be any one of the rings in magnet array 700 of FIG. 4, according to embodiments of the present invention.

FIG. 6 (I) shows a perspective drawing of a first exemplary theta magnetic ring 900a. In FIG. 6 (I), the theta magnetic ring comprises twenty cuboid magnetic segments 910. The magnetic moment of each segment 920 has a zero axial (Z) component and non-zero radial (r) and theta (θ) components, as illustrated by arrows 920.

FIG. 6 (II) shows a perspective drawing of a second exemplary theta magnetic ring 900b, comprising twenty cuboid magnetic segments 930. The magnetic moment of each segment 930 has a zero radial (r) component and non-zero axial (Z) and theta (θ) components, as illustrated by arrows 940.

FIG. 6 (III) shows a perspective drawing of a third exemplary theta magnetic ring 900c, comprising twenty cuboid magnetic segments 950. The magnetic moment of each segment 950 has non-zero radial (r), theta (θ) and axial (Z) components, as illustrated by arrows 960.

It will be appreciated that the above descriptions are intended only to serve as examples, and that many other embodiments are possible within the scope of the present invention. For example, magnet array 700 may be combined with either a static or dynamic shimming system, to further improve field uniformity inside imaging volume 730. In addition, the presented magnet array is asymmetric however, the theta rings may be used also in symmetric arrays or any other type of magnetic array, with or without a yoke to enhance their uniformity.

In addition, it is possible to combine the described array (having multiple rings coaxial with a common axis) with one or more additional ring arrays for which the rings are coaxial with one or more different axes which are at an angle from the first longitudinal common axis. The combination of arrays jointly creates a magnetic field in an arbitrary direction in space. The additional ring arrays may also contain theta phase rings, those rings however are defined according to their own cylindrical coordinate system with a z' axis defined as their own common coaxiality axis.

It is possible, for example, to have two arrays of rings with coaxiality axes that differ by 45 degrees from one another. Each array may contain one or more theta rings and may be optimized to obtain a field substantially uniform in the inner volume along each of the array axes. The combination of the two arrays results in a homogeneous magnetic field in a direction which is between the first and second longitudinal axes.

When dynamic shimming or gradient pulse fields are used, segmented rings are preferred with the presence of electrically insulating material in the gaps between adjacent magnet elements so as to minimize the deleterious effects of eddy currents on field uniformity. Furthermore, magnet array 700 may be combined with resistive coils placed concentric to the Z-axis, in order to enhance the magnetic field strength inside their respectively defined inner volumes.

Although the embodiments described herein mainly address mobile MRI application, the methods and systems described herein can also be used in other applications, such as aerospace applications, that require strong, uniform and lightweight magnets such as scanning electron microscopes (SEM).

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A magnet array for use in a brain Magnetic Resonance Imaging (MRI) system, the magnet array comprising:
   multiple magnet elements, which are made of a permanent magnet material, and which are dispersed around a longitudinal axis passing through a predefined imaging volume of the MRI system, wherein a group of at least some of the magnet elements encircle the imaging volume, wherein the magnet elements are divided into (i) a first assembly characterized by a first minimal inner radius that is smallest among distances between the magnet elements of the first assembly and the longitudinal axis, and (ii) a second assembly positioned on a first side the imaging volume and alongside the first assembly along the longitudinal axis and characterized by a second minimal inner radius that is smallest among the distances between the magnet elements of the second assembly and the longitudinal axis, wherein the first minimal inner radius of the first assembly is larger than the second minimal inner radius of the second assembly, wherein a center of the imaging volume is located outside the second assembly, and wherein at least one of the magnet elements in the first assembly is located on a second side of the imaging volume, the magnet elements configured to jointly generate a magnetic field of at least a given level of uniformity inside the imaging volume; and
   a frame, which is configured to fixedly hold the multiple magnet elements in place.

2. The magnet array according to claim 1, wherein the magnetic field generated by the array is along a direction parallel to the longitudinal axis.

3. The magnet array according to claim 1, wherein the magnet elements are arranged with reflectional asymmetry with respect to the longitudinal axis.

4. The magnet array according to claim 1, wherein the magnet elements are grouped to form magnet rings coaxial with the longitudinal axis, and wherein each magnet ring has a rotational symmetry with respect to an in-plane rotation of the magnet ring around the longitudinal axis.

5. The magnet array according to claim 1, wherein the imaging volume is an ellipsoid of revolution around the longitudinal axis.

6. The magnet array according to claim 1, wherein the magnet elements are pre-magnetized with magnetization directions that maximize uniformity of the magnetic field inside the imaging volume.

7. The magnet array according to claim 1, wherein the magnet elements are pre-magnetized with magnetization directions that minimize a fringe field outside the magnet array.

8. The magnet array according to claim 1, wherein the magnet elements are electrically insulated from each other.

9. The magnet array according to claim 1, wherein each of the magnet elements has a shape that is one of a sphere, a cylinder, an ellipsoid, a polygonal prism and a solid ring.

10. The magnet array according to claim 1, wherein the magnet elements are separated from each other by at least one non-magnetic element comprising a solid, gas or liquid.

11. The magnet array according to claim 1, wherein at least two magnet elements have magnetization vectors in directions different by more than 45 degrees from one another.

12. A method for producing a magnet array for use in a brain Magnetic Resonance Imaging (MRI) system, the method comprising:
   positioning multiple magnet elements, which are made of a permanent magnet material, and which are dispersed around a longitudinal axis passing through a predefined imaging volume of the MRI system, wherein a group of at least some of the magnet elements encircle the imaging volume, wherein the magnet elements are divided into (i) a first assembly characterized by a first minimal inner radius that is smallest among distances between the magnet elements of the first assembly and the longitudinal axis, and (ii) a second assembly positioned on a first side of the imaging volume and alongside the first assembly along the longitudinal axis and characterized by a second minimal inner radius that is smallest among the distances between the magnet elements of the second assembly and the longitudinal axis, wherein the first minimal inner radius of the first assembly is larger than the second minimal inner radius of the second assembly, wherein a center of the imaging volume is located outside the second assembly, and wherein at least one of the magnet elements in the first assembly is located on a second side of the imaging volume, the magnet elements configured to jointly generate a magnetic field of at least a given level of uniformity inside the imaging volume; and fixedly holding the multiple magnet elements in place using a frame.

13. The method according to claim 12, wherein the magnetic field generated by the array is along a direction parallel to the longitudinal axis.

14. The method according to claim 12, wherein the magnet elements are arranged with reflectional asymmetry with respect to the longitudinal axis.

15. The method according to claim 12, wherein magnet elements are grouped to form magnet rings coaxial with the longitudinal axis, wherein each magnet ring has a rotational symmetry with respect to an in-plane rotation of the magnet ring around the longitudinal axis.

16. The method according to claim 12, wherein the imaging volume is an ellipsoid of revolution around the longitudinal axis.

17. The method according to claim 12, wherein the magnet elements are pre-magnetized with magnetization directions that maximize uniformity of the magnetic field inside the imaging volume.

18. The method according to claim 12, wherein the magnet elements are pre-magnetized with magnetization directions that minimize a fringe field outside the magnet array.

19. The method according to claim 12, wherein the magnet elements are electrically insulated from each other.

20. The method according to claim 12, wherein each of the magnet elements has a shape that is one of a sphere, a cylinder, an ellipsoid, a polygonal prism and a solid ring.

21. The method according to claim 12, wherein the magnet elements are separated from each other by at least one non-magnetic element comprising a solid, gas or liquid.

22. The method according to claim 12, wherein at least two magnet elements have magnetization vectors in directions different by more than 45 degrees from one another.

* * * * *